(12) United States Patent
Oshima et al.

(10) Patent No.: US 12,122,988 B2
(45) Date of Patent: Oct. 22, 2024

(54) CELL EVALUATION DEVICE AND CELL EVALUATION SYSTEM

(71) Applicant: SONY CORPORATION, Tokyo (JP)

(72) Inventors: Shiori Oshima, Kanagawa (JP); Koji Futamura, Tokyo (JP); Kenji Tanaka, Tokyo (JP); Tomoyuki Umetsu, Tokyo (JP); Masahiro Matsumoto, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 537 days.

(21) Appl. No.: 16/978,153

(22) PCT Filed: Jan. 17, 2019

(86) PCT No.: PCT/JP2019/001252
§ 371 (c)(1),
(2) Date: Sep. 3, 2020

(87) PCT Pub. No.: WO2019/176275
PCT Pub. Date: Sep. 19, 2019

(65) Prior Publication Data
US 2021/0040426 A1     Feb. 11, 2021

(30) Foreign Application Priority Data
Mar. 12, 2018   (JP) .................. 2018-044776

(51) Int. Cl.
*C12M 1/34*   (2006.01)
*G01N 21/76*   (2006.01)

(52) U.S. Cl.
CPC .............. *C12M 1/34* (2013.01); *G01N 21/76* (2013.01)

(58) Field of Classification Search
CPC ...... C12M 41/46; C12M 1/34; C12M 1/3453; C12M 1/3446
See application file for complete search history.

(56) References Cited

U.S. PATENT DOCUMENTS

| 2007/0166741 | A1* | 7/2007 | Heil ............... C12Q 1/6837 435/7.1 |
| 2011/0124520 | A1 | 5/2011 | Love et al. |

(Continued)

FOREIGN PATENT DOCUMENTS

| AU | 2012205147 A1 | 8/2012 |
| CN | 104321421 A | 1/2015 |

(Continued)

OTHER PUBLICATIONS

International Search Report and Written Opinion of PCT Application No. PCT/JP2019/001252, issued on Apr. 23, 2019, 09 pages of ISRWO.

*Primary Examiner* — Jonathan M Hurst
(74) *Attorney, Agent, or Firm* — CHIP LAW GROUP

(57) ABSTRACT

To provide a cell evaluation device capable of evaluating cells and a secretory substance emitted from the cells accurately and precisely. Provided is a cell evaluation device including a first capturing unit that captures a secretory substance secreted by cells, and an image acquisition unit that acquires an image obtained by imaging observation light of the cells and light emitted from a luminescent substance bonded to the secretory substance, in which the image acquisition unit and the first capturing unit are disposed in this order, and the image acquisition unit acquires position information for the cells and the secretory substance.

15 Claims, 10 Drawing Sheets

(56) References Cited

U.S. PATENT DOCUMENTS

| | | | |
|---|---|---|---|
| 2012/0032235 A1 | 2/2012 | Bikumandla | |
| 2015/0204862 A1 | 7/2015 | Fan et al. | |
| 2018/0217146 A1 | 8/2018 | Varadarajan et al. | |
| 2018/0246089 A1* | 8/2018 | Chou | B01L 3/5055 |
| 2020/0156071 A1* | 5/2020 | Hansen | G01N 33/54366 |

FOREIGN PATENT DOCUMENTS

| | | | |
|---|---|---|---|
| CN | 105579847 A | 5/2016 | |
| CN | 105866105 A | 8/2016 | |
| EP | 2297333 A1 | 3/2011 | |
| EP | 2888349 A1 | 7/2015 | |
| EP | 3274720 A1 | 1/2018 | |
| EP | 3341728 A1 | 7/2018 | |
| EP | 3362795 A1 | 8/2018 | |
| JP | 2007-263701 A | 10/2007 | |
| JP | 2011-521644 A | 7/2011 | |
| JP | 2015-527588 A | 9/2015 | |
| JP | 2017-063716 A | 4/2017 | |
| JP | 2018-514195 A | 6/2018 | |
| JP | 2018-532998 A | 11/2018 | |
| WO | 2009/145925 A1 | 12/2009 | |
| WO | 2014/031997 A1 | 2/2014 | |
| WO | 2016/154620 A1 | 9/2016 | |
| WO | 2017/048871 A1 | 3/2017 | |
| WO | 2017/056362 A1 | 4/2017 | |

* cited by examiner

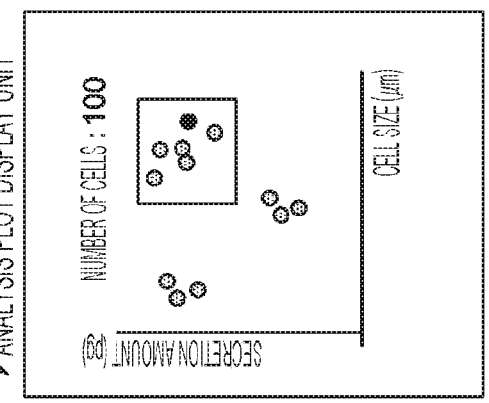
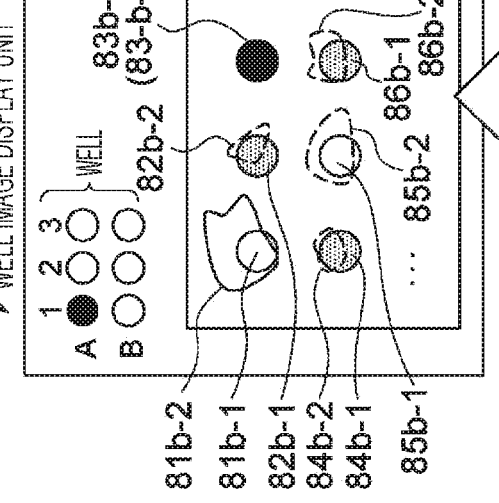
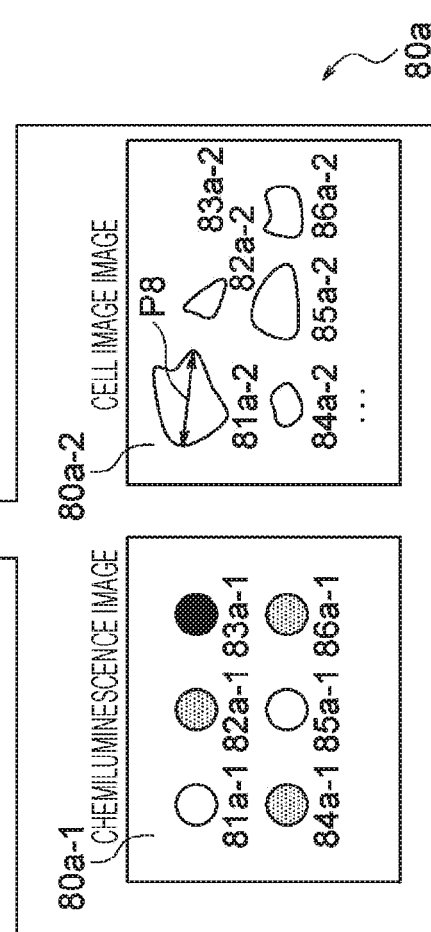

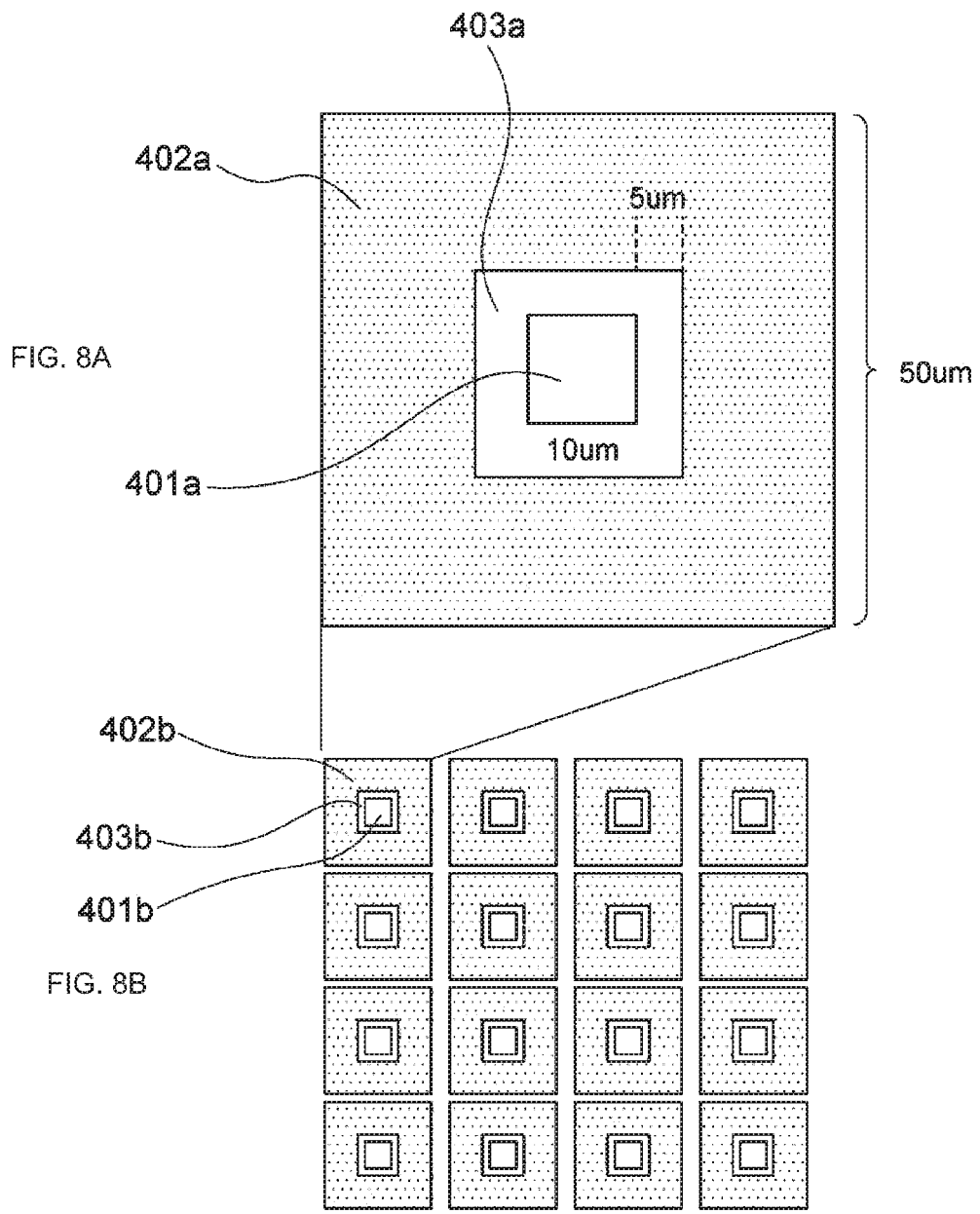

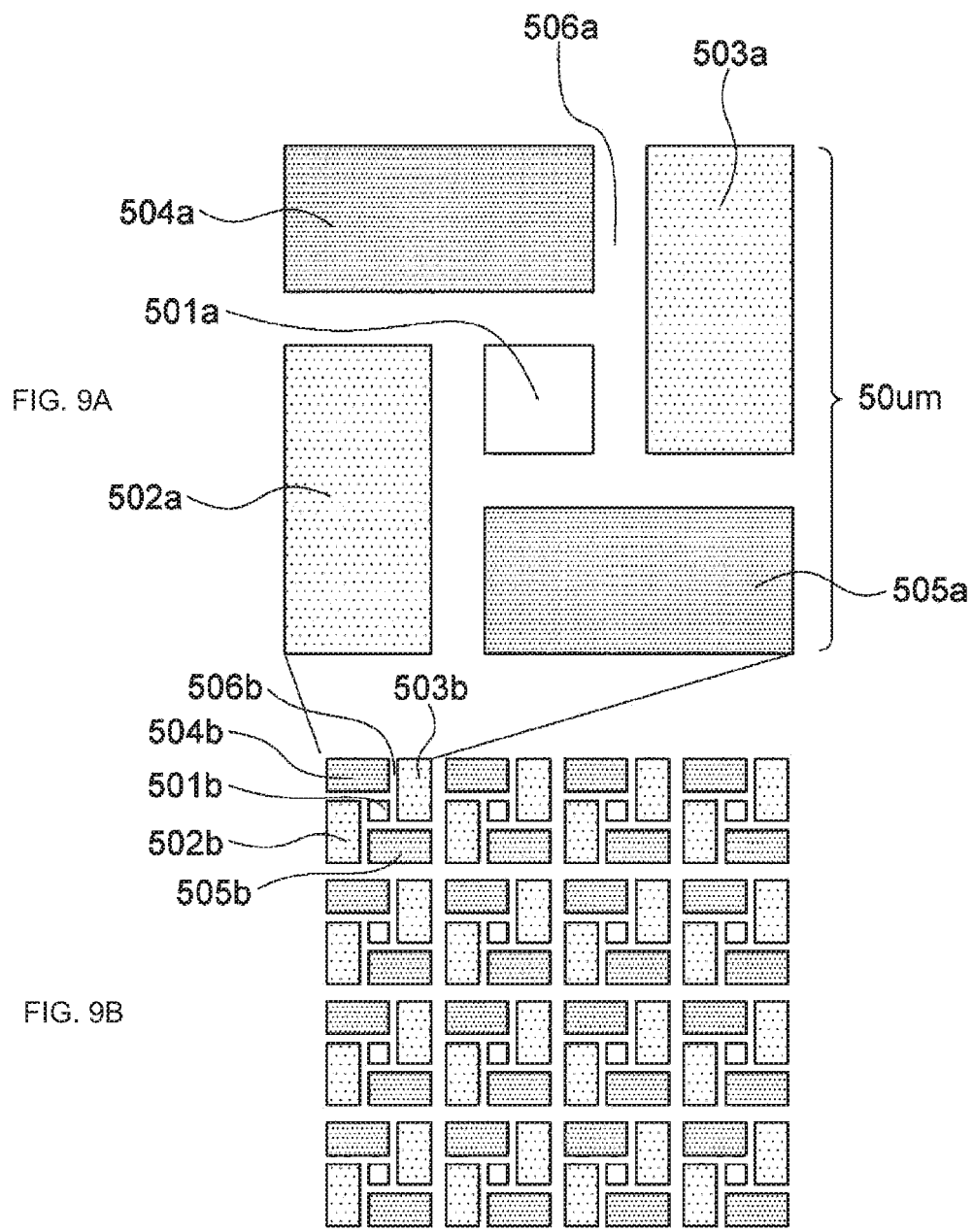

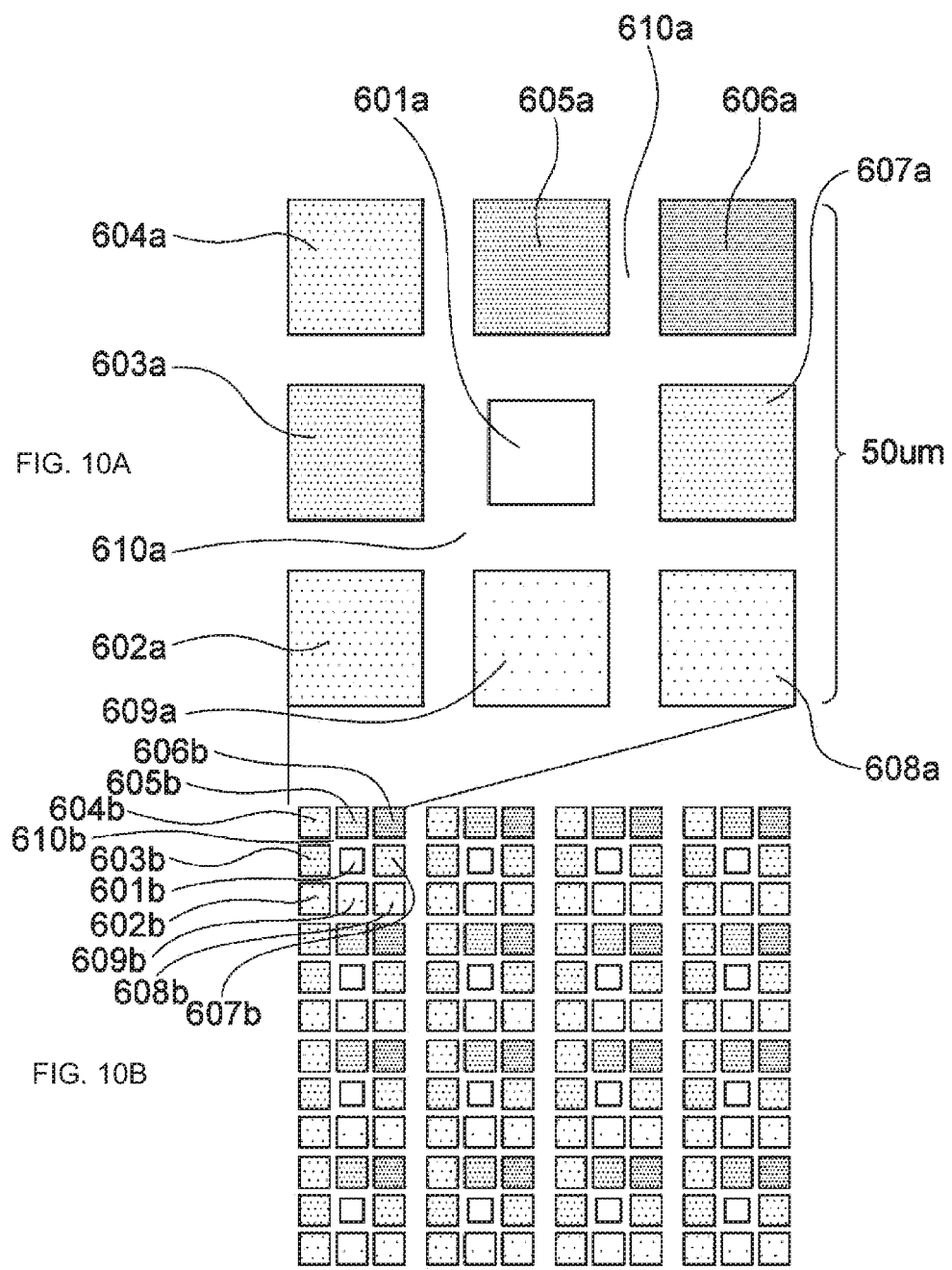

CELL EVALUATION DEVICE AND CELL EVALUATION SYSTEM

CROSS REFERENCE TO RELATED APPLICATIONS

This application is a U.S. National Phase of International Patent Application No. PCT/JP2019/001252 filed on Jan. 17, 2019, which claims priority benefit of Japanese Patent Application No. JP 2018-044776 filed in the Japan Patent Office on Mar. 12, 2018. Each of the above-referenced applications is hereby incorporated herein by reference in its entirety.

TECHNICAL FIELD

The present technology relates to a cell evaluation device and a cell evaluation system.

BACKGROUND ART

In recent years, a system that evaluates cells and a secretory substance emitted from the cells continue to develop, and various techniques have been proposed.

For example, a technique related to a complementary metal oxide semiconductor (CMOS) biosensor system has been proposed (see Patent Document 1).

CITATION LIST

Patent Document

Patent Document 1: US Patent Application Laid-Open No. 2012/0032235

SUMMARY OF THE INVENTION

Problems to be Solved by the Invention

However, with the technique proposed in Patent Document 1, it may be impossible to evaluate cells and a secretory substance emitted from the cells accurately and precisely.

Therefore, the present technology has been achieved in view of such a situation, and a main object of the present technology is to provide a cell evaluation device capable of evaluating cells and a secretory substance emitted from the cells accurately and precisely.

Solutions to Problems

The present inventor made intensive studies in order to solve the above object. As a result, surprisingly, the present inventor has succeeded in being able to evaluate cells and a secretory substance emitted from the cells accurately and precisely, and has completed the present technology.

That is, the present technology first provides a cell evaluation device including:
  a first capturing unit that captures a secretory substance secreted by cells; and
  an image acquisition unit that acquires an image obtained by imaging observation light of the cells and light emitted from a luminescent substance bonded to the secretory substance, in which
  the image acquisition unit and the first capturing unit are disposed in this order, and
  the image acquisition unit acquires position information for the cells and the secretory substance.

In the cell evaluation device according to the present technology, the image acquisition unit may be a CMOS image sensor.

In the cell evaluation device according to the present technology, the image acquisition unit can acquire an image obtained by imaging chemiluminescence emitted by a reaction of the luminescent substance that is an enzyme with a substrate.

In the cell evaluation device according to the present technology, the first capturing unit may include a molecule that is nonspecifically or specifically bonded to the secretory substance.

In the cell evaluation device according to the present technology, a protection unit may be disposed in a region where the first capturing unit does not include the molecule that is nonspecifically or specifically bonded to the secretory substance.

The molecule that is nonspecifically or specifically bonded to the secretory substance may be at least one selected from the group consisting of a first antibody, a first aptamer, and a molecular imprinted polymer, and a plurality of types of the first antibodies may be included.

The cell evaluation device according to the present technology may further include a second capturing unit that captures the cells, and the image acquisition unit and the second capturing unit may be disposed in this order in the cell evaluation device according to the present technology.

In the cell evaluation device according to the present technology, the first capturing unit may be disposed around the second capturing unit.

In the cell evaluation device according to the present technology, the second capturing unit may include a molecule that is nonspecifically or specifically bonded to the cells.

In the cell evaluation device according to the present technology, a protection unit may be disposed in a region where the second capturing unit does not include the molecule that is nonspecifically or specifically bonded to the cells.

The molecule that is nonspecifically or specifically bonded to the cells may be at least one selected from the group consisting of a second antibody, a second aptamer, a supramolecule, and oleylamine, and a plurality of types of the second antibodies may be included.

In the cell evaluation device according to the present technology, a photodegradable linker may be included between the second capturing unit and the image acquisition unit.

Furthermore, the present technology provides a cell evaluation device including:
  a first capturing unit that captures a secretory substance secreted by cells;
  an image acquisition unit that acquires an image obtained by imaging observation light of the cells and light emitted from a luminescent substance bonded to the secretory substance; and
  an analysis unit that analyzes the obtained image, in which
  the image acquisition unit and the first capturing unit are disposed in this order, and
  the image acquisition unit acquires position information for the cells and the secretory substance.

In the cell evaluation device according to the present technology, the analysis unit can quantify the secretory substance on the basis of the intensity of the light emitted from the luminescent substance bonded to the secretory substance.

The analysis unit can analyze the cells on the basis of brightness information of the observation light of the cells and/or the light emitted from the luminescent substance bonded to the secretory substance.

The cell evaluation device according to the present technology may further include an irradiation unit that projects light onto the cells.

The cell evaluation device according to the present technology may further include a display unit that displays the image.

The display unit may include: a well image display unit based on a cell image image obtained by imaging observation light of the cells and a chemiluminescence image obtained by imaging light emitted from a luminescent substance bonded to the secretory substance; and an analysis data display unit and an analysis plot display unit based on analysis of the analysis unit.

Moreover, the present technology provides a cell evaluation system including:
 a first capturing unit that captures a secretory substance secreted by cells;
 an image acquisition unit that acquires an image obtained by imaging observation light of the cells and light emitted from a luminescent substance bonded to the secretory substance; and
 an analysis unit that analyzes the obtained image, in which
 the image acquisition unit and the first capturing unit are disposed in this order, and
 the image acquisition unit acquires position information for the cells and the secretory substance.

Furthermore, the present technology provides a cell evaluation device including:
 a first antibody that captures a secretory substance secreted by cells;
 a second antibody that captures the cells; and
 a CMOS image sensor that acquires an image obtained by imaging observation light of the cells and light emitted from a luminescent substance bonded to the secretory substance, in which
 the CMOS image sensor, the first antibody, and the second antibody are disposed in this order,
 the first antibody is disposed around the second antibody, and
 the CMOS image sensor acquires position information for the cells and the secretory substance, and
provides a cell evaluation device including:
 a first antibody that captures a secretory substance secreted by cells;
 a second antibody that captures the cells;
 a CMOS image sensor that acquires an image obtained by imaging observation light of the cells and light emitted from a luminescent substance bonded to the secretory substance; and
 an analysis unit that analyzes the acquired image, in which
 the CMOS image sensor, the first antibody, and the second antibody are disposed in this order,
 the first antibody is disposed around the second antibody, and
 the CMOS image sensor acquires position information for the cells and the secretory substance.

Effects of the Invention

According to the present technology, cells and a secretory substance emitted from the cells can be evaluated accurately and precisely. Note that the effects described here are not necessarily limited, and may be any of the effects described in the present disclosure.

BRIEF DESCRIPTION OF DRAWINGS

FIGS. 6A, 6B, 6C, and 6D are diagrams illustrating a configuration example of a display unit.

FIGS. 8A and 8B are diagrams illustrating an example of patterning of a first capturing unit and a second capturing unit.

FIGS. 9A and 9B are diagrams illustrating an example of patterning of a first capturing unit and a second capturing unit.

FIGS. 10A and 10B are diagrams illustrating an example of patterning of a first capturing unit and a second capturing unit.

MODE FOR CARRYING OUT THE INVENTION

Figure 1:
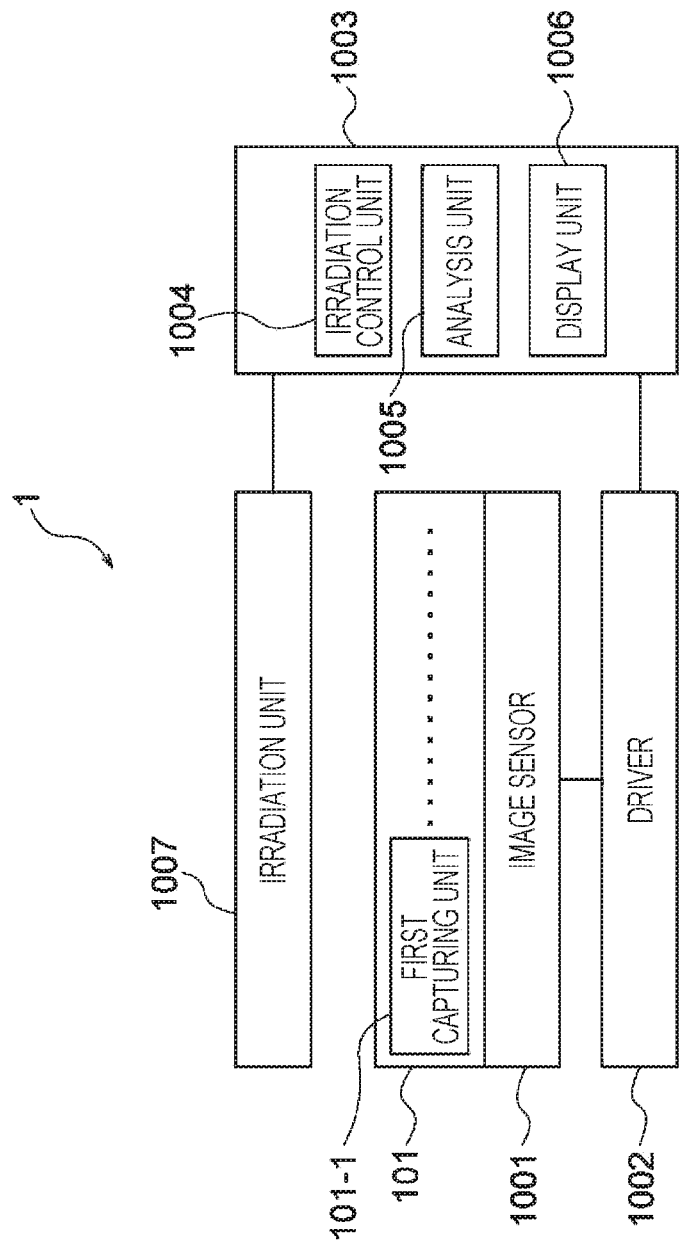
FIG. 1 is a block diagram illustrating a configuration example of a cell evaluation device according to a first embodiment to which the present technology is applied.

Hereinafter, a preferred embodiment for carrying out the present technology will be described. The embodiments described below exemplify representative embodiments of the present technology, and the scope of the present technology is not narrowly interpreted by the embodiments.

Note that the description will be made in the following order.

1. Overview of cell evaluation device according to the present technology
2. First embodiment (example 1 of cell evaluation device)
2-1. Cell evaluation device
2-2. First capturing unit
2-3. Image acquisition unit
2-4. Analysis unit
2-5. Irradiation unit
2-6. Display unit
3. Second embodiment (example 2 of cell evaluation device)
3-1. Cell evaluation device
3-2. First capturing unit and second capturing unit, and patterning of first capturing unit and second capturing unit
3-3. Image acquisition unit, analysis unit, irradiation unit, and display unit
4. Third embodiment (example of cell evaluation system)
4-1. Cell evaluation system
4-2. First capturing unit, second capturing unit, image acquisition unit, analysis unit, irradiation unit, and display unit

1. Overview of Cell Evaluation Device According to the Present Technology

An overview of a cell evaluation device according to the present technology will be described.

As a method for acquiring a secretory substance emitted from cells, methods called an ELISA method and an ELISPOT method, and a specialized system (for example, intracellular cytokine measurement system using flow cytometry, and the like) have already been widely used.

In the ELISA method, a large amount of cells are cultured in a well, the cells are removed, then only a secretory substance is collected, and the secretion amount is measured. In this case, it is not possible to find what percentage of the cells secreted the secretory substance. Therefore, for the purpose of paying attention to each of the cells, research and development have been performed in which cells are cultured in a smaller well in units of one to several cells and the secretion amount emitted by each of the cells is calculated.

Meanwhile, in the ELISPOT method, a large amount of cells are cultured in a well, a secretory substance emitted from the cells is captured with a membrane placed at a bottom of the well, the cells are removed, and then a reaction is caused with the secretory substance attached to the membrane to color the secretory substance. By counting the number of colored spots by microscopic observation, the number of cells that secreted the secretory substance can be calculated. However, by any one of the methods, it may be difficult to find which cell emitted the secretory substance, or it may be impossible to perform classification for each cell in coexistence of a plurality of cells. Thereafter, there has been proposed a method in which each single cell is put into a small well for measurement. However, since cells are put into wells, respectively, it is not possible to observe an interaction and the like in coexistence of a plurality of cells. Furthermore, in the ELISPOT method, since it is necessary to remove cells before measurement as described above, it is impossible to take out only specific cells after ELISPOT and then to perform post-analysis (gene analysis and the like).

The present technology has been achieved in view of the above situation, and it is possible to find which cell secreted what amount even in an environment where a plurality of cells coexists. As a result, it is possible to understand an interaction that occurs between different cells such as between cancer cells and immune cells, which has been difficult as an application.

Examples of a cell to be observed by the cell evaluation device according to the present technology include a cancer cell, an immune cell, and the like. Particularly, the immune cell includes a T cell, an NK cell, a macrophage, and the like. Furthermore, the cell also includes a tissue in which a single or a plurality of cells is assembled with a certain function. Moreover, examples of a secretory substance emitted from cells to observed by the cell evaluation device according to the present technology include IFN-γ, interleukin, chemokine, and the like.

Since the present technology can add at least quantification of a secretory substance for each of cells and imaging of the cells to the function of ELISPOT (counting the number of secretory cells), it is possible to identify a cell type that has emitted the secretory substance and a state thereof. For example, in co-culture of cancer cells and immune cells, at present, it is not found whether the cancer cells or the immune cells have emitted IFNγ, and it is desired to count only the number of live cells that have emitted IFNγ. It is possible to solve a problem that IFNγ is emitted also during apoptosis, for example. Since the present technology has at least the technology based on the ELISPOT method and the ELISA method, it is possible to reduce the number of blood samples required. Since cells can be collected in principle, it is possible to reanalyze only cells that have emitted a secretory substance. It is possible to evaluate which cells secreted what amount even in an environment where a plurality of cells coexists. That is, as described above, it is possible to understand an interaction that occurs between different cells such as between cancer cells and immune cells, which has been difficult.

Hereinafter, in order to specifically describe the cell evaluation device and the cell evaluation system according to the present technology, a first embodiment (example 1 of cell evaluation device) of the present technology, a second embodiment (example 2 of cell evaluation device) of the present technology, and a third embodiment (example of cell evaluation system) of the present technology will be described.

2. First Embodiment (Example 1 of Cell Evaluation Device)

2-1. Cell Evaluation Device

A cell evaluation device according to a first embodiment (example 1 of cell evaluation device) of the present technology is a cell evaluation device including: a first capturing unit that captures a secretory substance secreted by cells; and an image acquisition unit that acquires an image obtained by imaging observation light of the cells and light emitted from a luminescent substance bonded to the secretory substance, in which the image acquisition unit and the first capturing unit are disposed in this order, and the image acquisition unit acquires position information for the cells and the secretory substance.

Here, the phrase that the image acquisition unit and the first capturing unit are disposed in this order means that the image acquisition unit and the first capturing unit may be disposed continuously, or the image acquisition unit and the first capturing unit may be disposed via an optional material layer (which may be a material film, the same hereinafter) or a material unit. In addition, the phrase that the image acquisition unit and the first capturing unit are disposed continuously means that the first capturing unit is disposed immediately above the image acquisition unit. Furthermore, the phrase that the first capturing unit is disposed immediately above the image acquisition unit means that, for example, the first capturing unit is disposed at a position 150 μm or less apart from the image acquisition unit, preferably at a position 10 μm or less apart from the image acquisition unit.

The cell evaluation device according to the first embodiment of the present technology can further include at least one of an analysis unit, an irradiation unit, or a display unit. That is, the cell evaluation device according to the first embodiment of the present technology can further include the analysis unit, can further include the irradiation unit, can further include the display unit, can further include the analysis unit and the irradiation unit, can further include the analysis unit and the display unit, can further include the irradiation unit and the display unit, or can further include the analysis unit, the irradiation unit, and the display unit.

Figure 2:
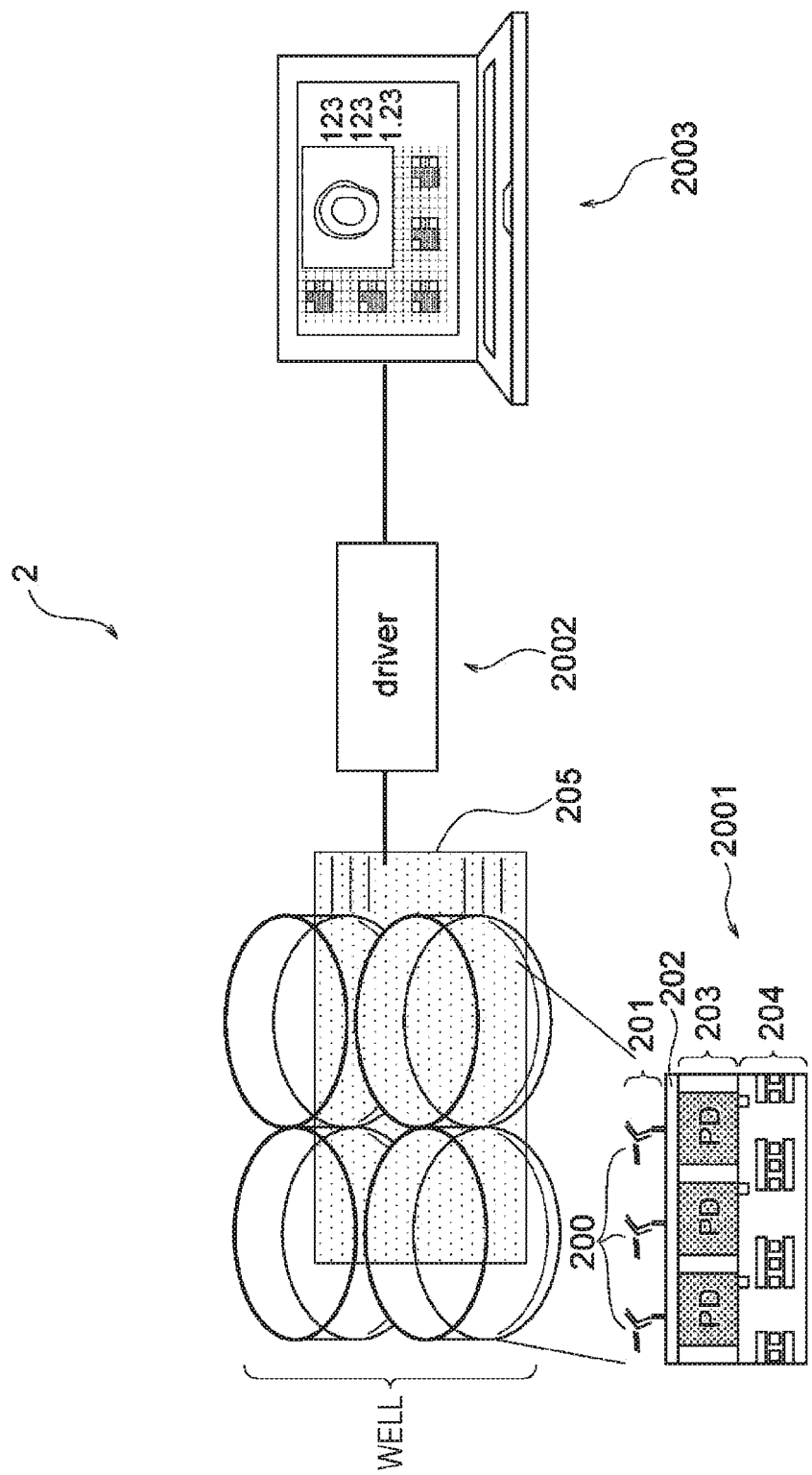
FIG. 2 is a diagram illustrating a configuration example of the cell evaluation device according to the first embodiment to which the present technology is applied.
Figure 3:
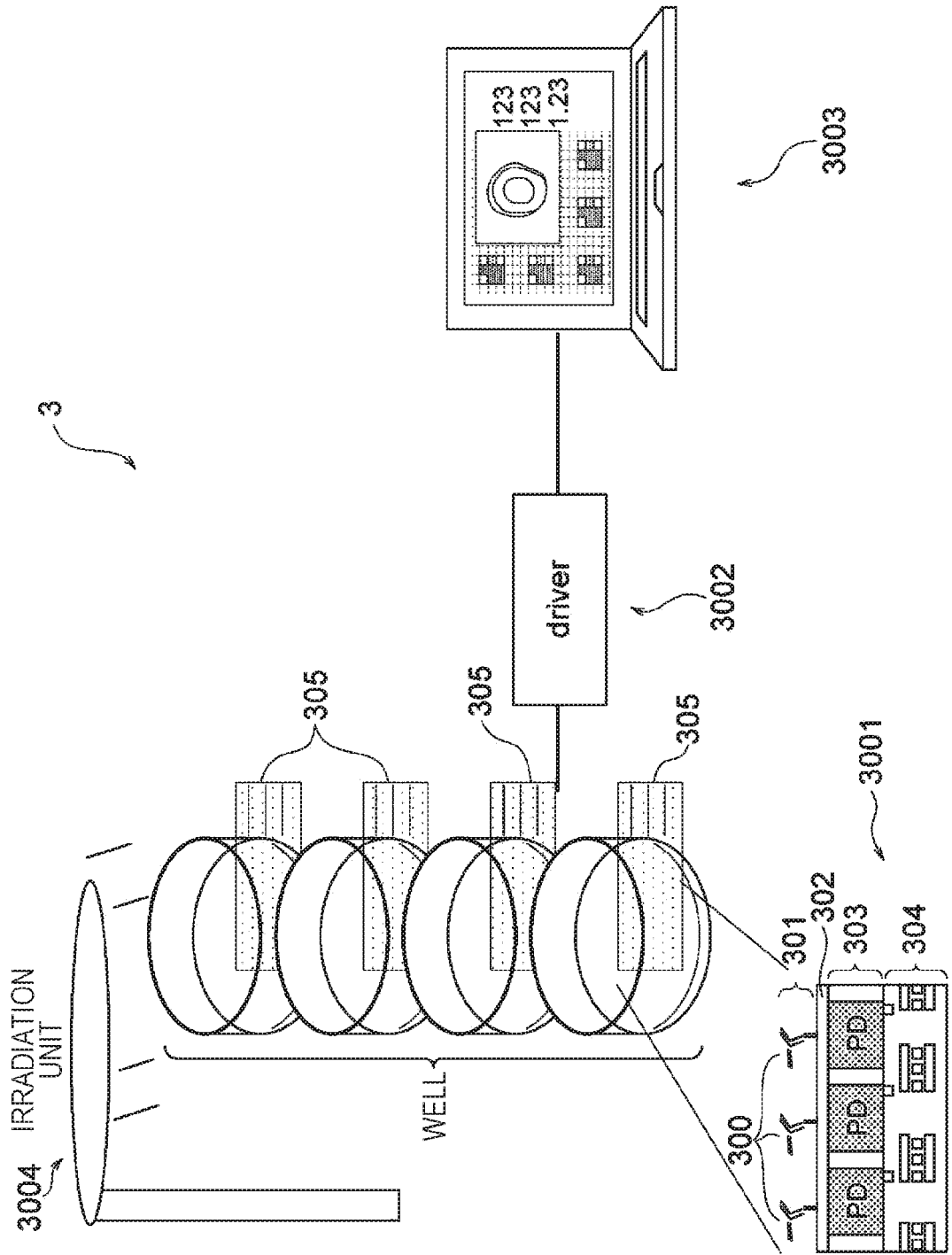
FIG. 3 is a diagram illustrating a configuration example of the cell evaluation device according to the first embodiment to which the present technology is applied.

A specific example of the cell evaluation device according to the first embodiment of the present technology will be described with reference to FIGS. 1 to 3. FIG. 1 is a block diagram illustrating an example of the cell evaluation device according to a first embodiment of the present technology. FIGS. 2 and 3 are configuration diagrams each illustrating an example of the cell evaluation device according to the first embodiment of the present technology.

First, refer to FIG. 1. A cell evaluation device 1 includes at least an image sensor upper portion 101 including a first capturing unit 101, an image sensor 1001 (for example, a CMOS image sensor) that is an image acquisition unit, and an analysis unit 1005. In addition, the cell evaluation device 1 further includes a driver 1002, an irradiation control unit 1004, a display unit 1006, and an irradiation unit 1007. As illustrated in FIG. 1, the irradiation control unit 1004, the analysis unit 1005, and the display unit 1006 may be formed as one device 1003. Although not illustrated in FIG. 1, the image sensor upper portion 101 may include a protection unit in addition to the first capturing unit 101. The irradiation control unit 1004 can control wavelength selectivity (light color selectivity) of light emitted by the irradiation unit 1007 and light exposure time.

In the cell evaluation device 1, the first capturing unit 101-1 (for example, a capturing unit including a first antibody for capturing a secretory substance) is disposed above the image sensor 1001 in a desired positional relationship. To identify cells, a cell image is captured using observation light of the cells or the irradiation unit 1007, and a cell size and a cell shape can be image-analyzed. A cell type and a cell state (for example, whether a cell is living or dead) can be accurately found. Furthermore, the irradiation unit can include a digital mirror device (DMD) and the like to control an irradiation position.

In addition, cells are cultured above the image sensor 1001, and a secretory substance emitted from the cells is captured by the first capturing unit 101-1 (for example, a capturing unit including a first antibody for capturing the secretory substance). Thereafter, by further causing a reaction with a chemiluminescent substance and the like, weak light is generated, and the light can be acquired by the image sensor 1001 immediately below the first capturing unit 101-1. The chemiluminescent substance is, for example, an enzyme, and chemiluminescence is emitted by a reaction of the enzyme with a substrate.

The weak light is photoelectrically converted into an electric signal by the driver 1002, and the brightness of only a sensor portion where the secretory substance has been captured is increased. Therefore, the position where the secretory substance has been obtained above the image sensor 1001 can be mapped. Since a positional relationship between the first capturing unit 101-1 (for example, a capturing unit including a first antibody for capturing the secretory substance) and cells can be designated in advance, a cell that has emitted the secretory substance can also be identified. Furthermore, the analysis unit 1005 can also quantify a secretory substance by utilizing a change in brightness depending on the concentration of the secretory substance. An image obtained from the image sensor 1001 is displayed on the display unit 1006 (for example, a monitor) through the analysis unit 1005.

Examples of measures for increasing sensitivity include an increase in the density of the first antibody for capturing the secretory substance included in the first capturing unit 101-1, minimizing a distance between the image sensor 1001 and the first capturing unit 101-1 (for example, an antibody layer) (disposing the first capturing unit 101-1 immediately above the image sensor 1001), an increase in exposure time, and separating a background noise portion and a signal portion from each other by image processing. In addition, acquisition of a cell image and detection of the secretory substance can also be performed in real time above the image sensor 1001.

Next, refer to FIG. 2. A cell evaluation device 2 includes an antibody layer (first capturing unit) 201 including an antibody (first antibody) 200, a CMOS image sensor 2001 that is an image acquisition unit, a driver 2002, and a device 2003 including an analysis unit and a display unit. Note that, in FIG. 2, the CMOS image sensor 2001 is illustrated for three pixels.

The CMOS image sensor 2001 includes a protective layer 202, a semiconductor substrate 203, and a wiring layer 204 in order from a light incident side. Photodiodes (PD) (three photodiodes (PD) in FIG. 2) are formed in the semiconductor substrate 203. Immediately above the protective layer 202 (upward from the protective layer in FIG. 2), the antibody layer 201 is disposed. By disposing the antibody layer 201 immediately above the protective layer 202, the CMOS image sensor 2001 can efficiently receive light emitted from a luminescent substance bonded to a secretory substance captured by the antibody 200 included in the antibody layer 201, and observation light of cells. The observation light of cells means, for example, light obtained by projecting natural light or room light onto the cells.

In FIG. 2, four wells (two wells in the horizontal direction and two wells in the vertical direction in FIG. 2) are illustrated, which means that four wells are disposed immediately above the one CMOS image sensor 2001 (a protective layer 205 included in the CMOS image sensor 2001) in the cell evaluation device 2. In each of the wells, for example, the antibody 200 that captures a secretory substance is immobilized on a collagen coat (protection unit), pretreated cells are trapped, the cells are stimulated and cultured, a secretory substance is emitted from the cells, and the secretory substance is captured by the antibody 200.

Moreover, refer to FIG. 3. A cell evaluation device 3 includes an antibody layer (first capturing unit) 301 including an antibody 300, a CMOS image sensor 3001 that is an image acquisition unit, a driver 3002, a device 3003 including an analysis unit and a display unit, and an irradiation unit 3004. Note that in FIG. 3, the CMOS image sensor 3001 is illustrated for three pixels.

The CMOS image sensor 3001 includes a protective layer 302, a semiconductor substrate 303, and a wiring layer 304 in order from a light incident side. Photodiodes (PD) (three photodiodes (PD) in FIG. 3) are formed in the semiconductor substrate 303. Immediately above the protective layer 302 (upward from the protective layer in FIG. 3), the antibody layer 301 is disposed. By disposing the antibody layer 301 immediately above the protective layer 302, the CMOS image sensor 3001 can efficiently receive light emitted from a luminescent substance bonded to a secretory substance captured by the antibody 300 included in the antibody layer 301, and light obtained by projection of light onto cells by the irradiation unit 3004.

In FIG. 3, four wells (four wells in the vertical direction in FIG. 3) are illustrated, which means that one well is disposed immediately above the one CMOS image sensor 3001 (a protective layer 305 included in the CMOS image sensor 3001) in the cell evaluation device 3. That is, the cell evaluation device 3 requires at least four CMOS image sensors 3001. In each of the wells, for example, the antibody 300 that captures a secretory substance is immobilized on a collagen coat (protection unit), pretreated cells are trapped, the cells are stimulated and cultured, a secretory substance is emitted from the cells, and the secretory substance is captured by the antibody 300.

2-2. First Capturing Unit

The cell evaluation device according to the first embodiment of the present technology includes the first capturing unit. As described above, the first capturing unit captures a secretory substance secreted by cells. The first capturing unit can include a molecule that is nonspecifically or specifically bonded to the secretory substance. The molecule that is nonspecifically or specifically bonded to the secretory substance may be at least one selected from the group consisting of a first antibody, a first aptamer, and an imprinted polymer, and a plurality of types of the first antibodies may be included. A protection unit can be disposed in a region where the first capturing unit does not include the molecule that is nonspecifically or specifically bonded to the secretory substance. The protection unit may include, for example, a collagen coat as described above. Furthermore, the protection unit may include at least one type of hydrophilic polymer capable of suppressing adsorption of a biopolymer. Examples of the hydrophilic polymer include polyethylene glycol, a polymer having a phosphorylcholine group in a side chain thereof, a polysaccharide, a polypeptide, and the like.

2-3. Image Acquisition Unit

The cell evaluation device according to the first embodiment of the present technology includes the image acquisition unit. The image acquisition unit may be, for example, an image sensor, and the image sensor may be, for example, a complementary metal oxide semiconductor (CMOS) image sensor or a solid-state imaging element such as a charge coupled device (CCD). Hereinafter, a back-illuminated solid-state imaging element and a front-illuminated solid-state imaging element which are examples of the CMOS image sensor will be described in detail.

Back-Illuminated Solid-State Imaging Element

Figure 4:
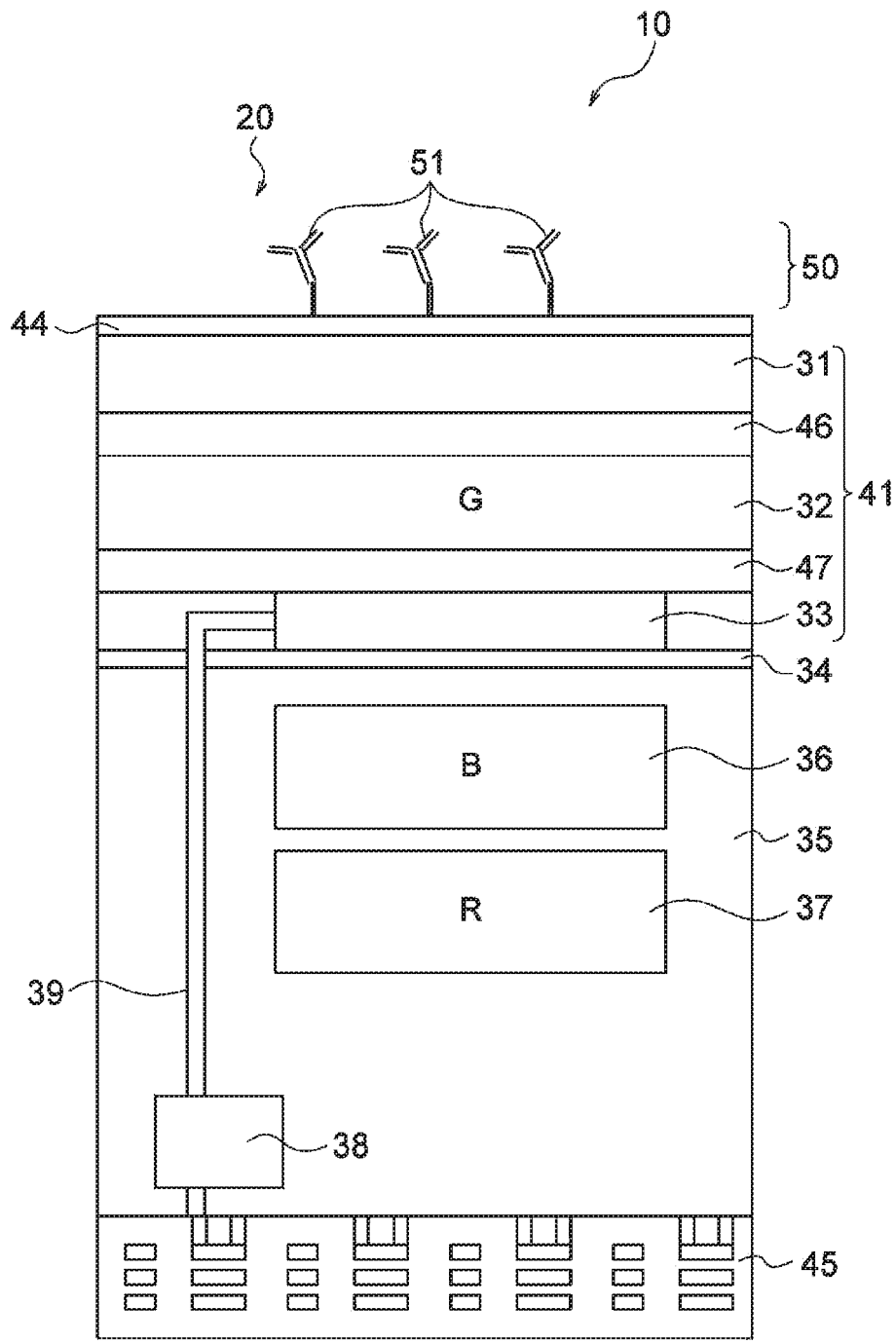
FIG. 4 is a cross-sectional view illustrating a configuration example of a CMOS image sensor (solid-state imaging element) including an antibody layer.

A back-illuminated solid-state imaging element, which is an example of the CMOS image sensor, will be described with reference to FIG. 4. FIG. 4 is a cross-sectional view illustrating a configuration example of one pixel 20 of a back-illuminated solid-state imaging element 10.

The pixel 20 includes, in one pixel, one organic photoelectric conversion element 41 and photodiodes 36 and 37 each having a pn junction, stacked in a depth direction. In addition, on the organic photoelectric conversion element 41 on a back surface side of a semiconductor substrate 35 (upper side in FIG. 4), a protective layer 44 is formed. Immediately above the protective layer 44, an antibody layer 50 including an antibody 51 is formed. That is, the protective layer 44 and the antibody layer 50 are continuously disposed. In this case, the thickness of the protective layer 44 may be as thin as 100 nm, for example. The protective layer 44 disposed continuously with the antibody layer 50 preferably has transparency in order to efficiently take light into the organic photoelectric conversion element 41 and the photodiodes 36 and 37. The protective layer 44 preferably contains $SiO_2$, for example. The pixel 20 includes the semiconductor substrate (silicon substrate) 35 in which the photodiodes 36 and 37 are formed. A light-receiving surface on which light is incident is formed on a back surface side of the semiconductor substrate 35 (upper side of the semiconductor substrate 35 in FIG. 4). A circuit including a read circuit or the like is formed on a front surface side of the semiconductor substrate 35. That is, the pixel 20 includes the light-receiving surface on a back surface side of the substrate 35 and a circuit-forming surface formed on a substrate front surface side opposite to the light-receiving surface. The semiconductor substrate 35 may be constituted by a first conductivity type, for example, an n-type semiconductor substrate.

In the semiconductor substrate 35, an inorganic photoelectric conversion unit having two pn junctions, that is, the first photodiode 36 and the second photodiode 37 are formed so as to be stacked in a depth direction from a back surface side. In the semiconductor substrate 35, the first photodiode 36 is formed, and the second photodiode 37 is formed in a depth direction from a back surface side (downward in the drawing). In FIG. 4, the first photodiode 36 is for blue (B), and the second photodiode 37 is for red (R).

Above a back surface of the semiconductor substrate 35 in a region where the first photodiode 36 and the second photodiode 37 are formed, an organic photoelectric conversion element 41 for first color is disposed in which a first electrode (lower electrode) 33, a first buffer layer 47, a photoelectric conversion layer 32, a second buffer layer 46, and a second electrode (upper electrode) 31 are stacked in this order. In the example of the back-illuminated solid-state imaging element 10 illustrated in FIG. 4, the organic photoelectric conversion element 41 is for green (G). The second electrode (upper electrode) 31 and the first electrode (lower electrode) 33 may be each constituted by, for example, a transparent conductive film such as an indium tin oxide film or an indium zinc oxide film.

As a combination of colors, in the example of the back-illuminated solid-state imaging element 10 illustrated in FIG. 4, the organic photoelectric conversion element 41 is for green, the first photodiode 36 is for blue, and the second photodiode 37 is for red. However, another color combination can be used. For example, the organic photoelectric conversion element 41 can be for red or blue, and the first photodiode 36 and the second photodiode 37 can be for other corresponding colors. In this case, the positions of the first photodiode 36 and the second photodiode 37 in the depth direction are set according to colors.

Furthermore, without using the first photodiode 36 and the second photodiode 37, three photoelectric conversion elements, that is, an organic photoelectric conversion element 41B for blue, an organic photoelectric conversion element 41G for green, and an organic photoelectric conversion element 41R for red may be applied to a solid-state imaging element (a back-illuminated solid-state imaging element and a front-illuminated solid-state imaging element) according to a second embodiment of the present technology. As the organic photoelectric conversion element 41B for performing photoelectric conversion with blue wavelength light, an organic photoelectric conversion material containing a coumarin-based dye, tris-8-hydryxyquinoline Al (Alq3), a meracyanine-based dye, and the like can be used. As the organic photoelectric conversion element 41G for performing photoelectric conversion with green wavelength light, for example, an organic photoelectric conversion material containing a rhodamine-based dye, a meracyanine-based dye, quinacridone, or the like can be used. As the organic photoelectric conversion element 41R for performing photoelectric conversion with red wavelength light, an organic photoelectric conversion material containing a phthalocyanine-based dye can be used.

Moreover, in addition to the organic photoelectric conversion element 41B for blue, the organic photoelectric conversion element 41G for green, and the organic photoelectric conversion element 41R for red, an organic photoelectric conversion element 41UV for ultraviolet light and/or an organic photoelectric conversion element 41IR for infrared light may be applied to the solid-state imaging element (a back-illuminated solid-state imaging element and a front-illuminated solid-state imaging element) according to the second embodiment of the present technology. By disposing the photoelectric conversion element 41UV for ultraviolet light and/or the photoelectric conversion element 41IR for infrared light, light having a wavelength outside a visible light region can be detected.

Light emitted from a luminescent substance by being bonded to a secretory substance captured by the antibody 51 (first antibody) included in the antibody layer 50, observation light of cells, and projection light obtained by projection of light onto the cells by an irradiation unit may each have any wavelength band, and may be imaged using at least one of the organic photoelectric conversion element 41, the first photodiode 36, or the second photodiode 37 depending on colors (wavelength bands) of these types of light. For example, in the solid-state imaging element 10, if the light emitted from a luminescent substance by being bonded to a secretory substance is green light, imaging can be performed using the organic photoelectric conversion element 41. If the light emitted from a luminescent substance by being bonded to a secretory substance is blue light, imaging can be performed using the first photodiode 36. If the light emitted from a luminescent substance by being bonded to a secretory substance is red light, imaging can be performed using the first photodiode 37. Furthermore, for example, if the observation light of cells or the light obtained by projection of light onto the cells by an irradiation unit is achromatic light (for example, white light, gray light, or the like), imaging can be performed using all of the organic photoelectric conversion element 41, the first photodiode 36, and the second photodiode 37.

In the organic photoelectric conversion element 41, the first electrode (lower electrode) 33 is formed, and an insulating film 34 for dielectrically isolating the first electrode (lower electrode) 33 is formed below the first electrode (lower electrode) 33 in the drawing.

In the one pixel 20, wiring 39 connected to the first electrode (lower electrode) 33 and wiring (not illustrated) connected to the second electrode (upper electrode) 31 are formed. For example, in order to suppress short-circuiting with Si, the wiring 39 and the wiring connected to the second electrode (upper electrode) 31 can be formed with $SiO_2$, a tungsten (W) plug having a SiN insulating layer in a periphery thereof, a semiconductor layer by ion implantation, or the like. In the example of the back-illuminated solid-state imaging element illustrated in FIG. 2, since a signal charge is a hole, the wiring 39 is a p-type semiconductor layer in a case where the wiring 39 is formed with a semiconductor layer by ion implantation. As the wiring connected to the second electrode (upper electrode) 31, an n-type semiconductor layer can be used because the second electrode (upper electrode) 31 extracts an electron.

In this example, an n-type region 38 for charge accumulation is formed on a front surface side of the semiconductor substrate 35. This n-type region 38 functions as a floating diffusion portion of the photoelectric conversion element 41.

As the insulating film 34 on the back surface of the semiconductor substrate 35, a film having a negative fixed charge can be used. Examples of the film having a negative fixed charge include a hafnium oxide film. That is, the insulating film 34 may be formed so as to have a three-layer structure obtained by sequentially forming a silicon oxide film, a hafnium oxide film, and a silicon oxide film from the back surface.

A wiring layer 45 is formed on a front surface side (lower side in FIG. 4) of the semiconductor substrate 35. Note that although not illustrated, a color filter, a transparent filter, an ND filter, a white filter, a gray filter, and the like may be formed, or an on-chip lens may be formed in the back-illuminated solid-state imaging element 10.

Front-Illuminated Solid-State Imaging Element

The CMOS image sensor is not limited to the back-illuminated solid-state imaging element described above, and may be a front-illuminated solid-state imaging element. The front-illuminated solid-state imaging element will be described.

An example of the front-illuminated solid-state imaging element is different from the back-illuminated solid-state imaging element 10 described above only in that the wiring layer 92 formed below the semiconductor substrate 35 in the back-illuminated solid-state imaging element is formed between the organic photoelectric conversion element 41 and the semiconductor substrate 35 in the front-illuminated solid-state imaging element. The other points may be similar to those of the back-illuminated solid-state imaging element 10 described above, and description thereof is omitted here.

2-4. Analysis Unit

As described above, the cell evaluation device according to the first embodiment of the present technology can include an analysis unit. The analysis unit can quantify a secretory substance on the basis of the intensity of light emitted from a luminescent substance bonded to the secretory substance. Furthermore, the analysis unit can analyze cells on the basis of observation light of the cells or light obtained by projection of light onto the cells by an irradiation unit (brightness information). In the analysis unit, the projected image of the cells may be converted into a higher-resolution image by a hologram technique, a super-resolution technique, or the like to analyze the cells.

Figure 5A:
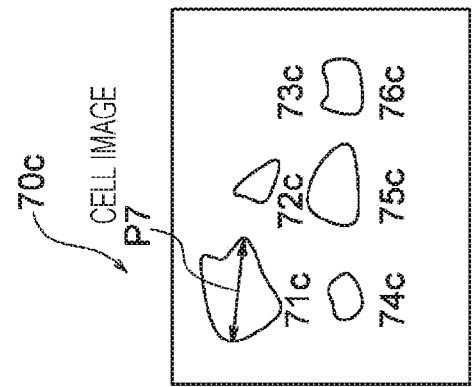
FIGS. 5A, 5B, and 5C are diagrams illustrating a configuration example of an analysis unit.
Figure 5B:
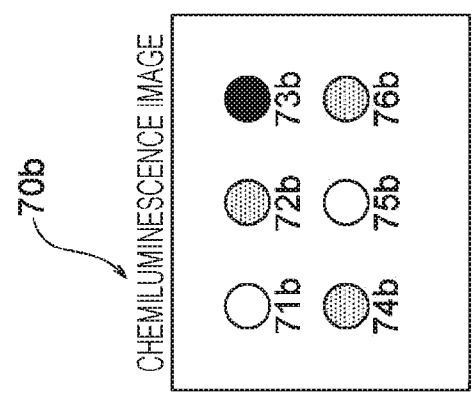
Figure 5C:
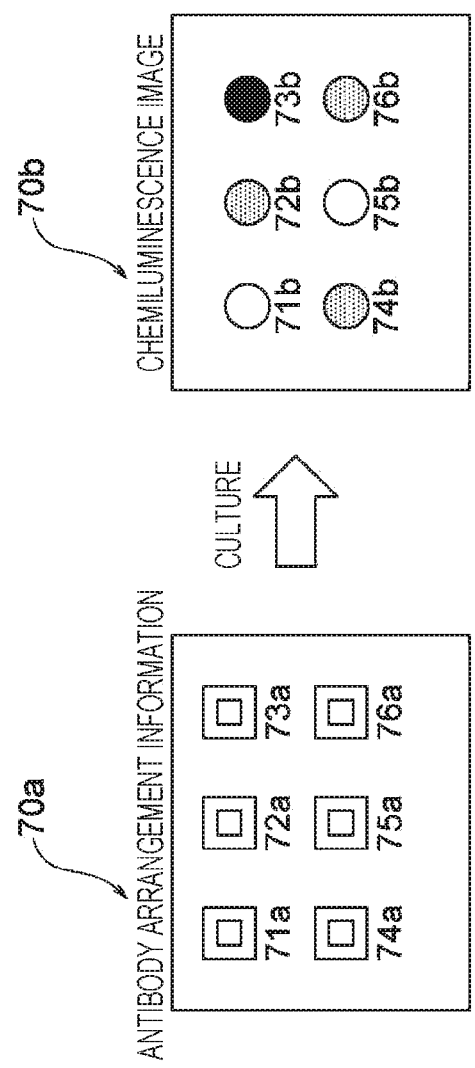

A specific configuration of the analysis unit will be described with reference to FIGS. 5A, 5B, and 5C. FIGS. 5A, 5B, and 5C illustrate a configuration example of the analysis unit. Specifically, FIG. 5A illustrates antibody arrangement information 70a, FIG. 5B illustrates a chemiluminescence image, and FIG. 5C illustrates a cell image.

Referring to FIG. 5A, the antibody arrangement information 70a indicates antibodies 71a to 76a. Each of the antibodies 71a to 76a includes, for example, a first antibody that has captured a secretory substance. In the case of the cell evaluation device according to the first embodiment of the present technology described later, each of the antibodies 71a to 76a includes, for example, a first antibody that has captured a secretory substance and a second antibody that has captured cells.

Referring to FIG. 5B, a chemiluminescence image 70b has individual chemiluminescence images 71b to 76b. The chemiluminescence images 71b to 76b correspond to the antibodies 71a to 76a, respectively. The chemiluminescence intensity can be calculated from brightness information in an antibody arrangement area of each of the chemiluminescence images 71b to 76b, and the amount of a secretory substance can be further calculated. Specifically, in quantification of a secretory substance, the intensity of chemiluminescence is acquired from brightness information for each pixel obtained from an image sensor, and the concentration of the secretory substance is calculated from the intensity and information of a calibration curve previously taken as data.

Referring to FIG. 5C, a cell image 70c indicates individual cell images 71c to 76c. In FIG. 5C, the cell images 71c to 76c are cell images having a magnification of one with respect to the cells (having the actual sizes of the cells), but may be cell images obtained by enlarging the cells or cell images obtained by reducing the cells as necessary. Since the cell images 71c to 76c correspond to the antibodies 71a to 76a and the chemiluminescence images 71b to 76b, respectively, the concentration of a secretory substance for each of the cell images 71c to 76c can be determined uniquely. Then, object segmentation is performed from brightness information of observation light of cells or the cell images 71c to 76c imaged on an image sensor by an irradiation unit. The size, position, and shape of each of the cell images 71c to 76c can be analyzed. An internal state of each of cells can be analyzed from a dynamic range inside each of the cells and the like. Moreover, the total number of cells included in one well can be calculated. For example, the size of a cell illustrated as the cell image 71c corresponds to an arrow P7. Note that in the case of the cell evaluation device according to the second embodiment of the present technology described later, since each of cells of the cell images 71c to 76c is a cell captured by the second antibody, cell position information is clearer.

2-5. Irradiation Unit

As described above, the cell evaluation device according to the first embodiment of the present technology can include an irradiation unit. The irradiation unit is one means for confirming a cell image, and as described above, can control wavelength selectivity of light emitted by the irradiation unit (selectivity of light color) and light exposure time using an irradiation control unit. Therefore, a sharper cell image can be obtained using the irradiation unit. Furthermore, it is also possible to release only specific cells by cleaving a photodegradable linker using a specific wavelength emitted.

2-6. Display Unit

The cell evaluation device according to the first embodiment of the present technology can include a display unit. The display unit includes: a well image display unit based on a cell image image obtained by imaging observation light of cells or light obtained by projection of light onto the cells by an irradiation unit (brightness information) and a chemiluminescence image obtained by imaging light emitted from a luminescent substance bonded to a secretory substance; and an analysis data display unit and an analysis plot display unit based on analysis of the analysis unit.

A specific configuration of the display unit will be described with reference to FIGS. 6A, 6B, 6C, and 6D. FIGS. 6A, 6B, 6C, and 6D illustrate a configuration example of the display unit. Specifically, FIG. 6B illustrates the well image display unit based on a chemiluminescence image 80a-1 and a cell image image 80a-2 illustrated in FIG. 6A. FIG. 6C illustrates the analysis data display unit. FIG. 6C illustrates the analysis plot display unit.

Referring to FIGS. 6A and 6B, an image combined by associating individual chemiluminescence images 81a-1 to 86a-1 of the chemiluminescence image 80a-1 with cell images 81a-2 to 86a-2, respectively, is illustrated in a well display unit 80b. FIG. 6B illustrates information regarding cells included in a well 1A out of a total of six wells 1A to 3A and 2A to 3B. Referring to FIG. 6B, a chemiluminescence image 81b-1 corresponds to a cell image 81b-2, a chemiluminescence image 82b-1 corresponds to a cell image 82b-2, a chemiluminescence image 83b-1 corresponds to a cell image 83b-2, a chemiluminescent image 84b-1 corresponds to a cell image 84b-2, a chemiluminescent image 85b-1 corresponds to a cell image 85b-2, and a chemiluminescent image 86b-1 corresponds to a cell image 86b-2. Among these images, a cell of the cell image 81a-2 (cell image 81b-2) having a cell size of arrow P8 has the largest cell size and the largest chemiluminescence amount among the six cells illustrated in FIG. 6B. In this case, the cell image 81a-2 is illustrated in white as a chemiluminescence image in FIGS. 6A and 6B. On the contrary, a cell of the cell image 83a-2 (cell image 83b-2) has the smallest cell size to such a level that the cell is not illustrated, and has a chemiluminescence amount of almost zero. In this case, the cell image 83a-2 is illustrated in black as a chemiluminescence image in FIGS. 6A and 6B.

Referring to FIG. 6C, an analysis data display unit 80c indicates that the total number of cells in the well 1A is 104, and also indicates the cell diameter (μm) of each cell (cell No.), secretion amount (pg) thereof, and the like.

Referring to FIG. 6D, an analysis plot display unit 80d indicates a graph in which the vertical axis represents a secretion amount (pg) and the horizontal axis represents a cell size (cell diameter) (μm). Referring to the graph illustrated in FIG. 6D, the number of cells to be evaluated can be determined to be 100 out of 104, as determined from a correlation between the secretion amount (pg) and the cell size (cell diameter) (μm). In FIG. 6D, a cell indicated by a black circle among the 100 cells corresponds to a cell of the cell image 81a-2 (cell image 81b-2) described above, for example.

3. Second Embodiment (Example 2 of Cell Evaluation Device)

3-1. Cell Evaluation Device

A cell evaluation device according to a second embodiment (example 2 of cell evaluation device) of the present technology is a cell evaluation device including: a first capturing unit that captures a secretory substance secreted by cells; a second capturing unit that captures the cells; and an image acquisition unit that acquires an image obtained by imaging observation light of the cells and light emitted from a luminescent substance bonded to the secretory substance, in which the image acquisition unit and the first capturing unit are disposed in this order, moreover the image acquisition unit and the second capturing unit are disposed in this order, and the image acquisition unit acquires position information for the cells and the secretory substance. That is, the cell evaluation device according to the second embodiment (example 2 of cell evaluation device) of the present technology has a configuration in which the second capturing unit is added to the cell evaluation device according to the first embodiment (example 1 of cell evaluation device) of the present technology. The configuration of the cell evaluation device according to the second embodiment (example 2 of cell evaluation device) of the present technology may be the same as that of the cell evaluation device according to the first embodiment (example 1 of cell evaluation device) of the present technology except the configuration of the second capturing unit. Here, the phrase that the image acquisition unit and the first capturing unit are disposed in this order means that the image acquisition unit and the first capturing unit may be disposed continuously, or the image acquisition unit and the first capturing unit may be disposed via an optional material layer (material film) or a material unit. In addition, the phrase that the image acquisition unit and the first capturing unit are disposed continuously means that the first capturing unit is disposed immediately above the image acquisition unit. The phrase that the first capturing unit is disposed immediately above the image acquisition unit means that, for example, the first capturing unit is disposed at a position 150 µm or less apart from the image acquisition unit, preferably at a position 10 µm or less apart from the image acquisition unit.

Furthermore, the phrase that the image acquisition unit and the second capturing unit are disposed in this order means that the image acquisition unit and the second capturing unit may be disposed continuously, or the image acquisition unit and the second capturing unit may be disposed via an optional material layer (material film) or a material unit. In addition, the phrase that the image acquisition unit and the second capturing unit are disposed continuously means that the second capturing unit is disposed immediately above the image acquisition unit. The phrase that the second capturing unit is disposed immediately above the image acquisition unit means that, for example, the second capturing unit is disposed at a position 150 µm or less apart from the image acquisition unit, preferably at a position 10 µm or less apart from the image acquisition unit.

The cell evaluation device according to the second embodiment of the present technology can further include at least one of an analysis unit, an irradiation unit, or a display unit. That is, the cell evaluation device according to the second embodiment of the present technology can further include the analysis unit, can further include the irradiation unit, can further include the display unit, can further include the analysis unit and the irradiation unit, can further include the analysis unit and the display unit, can further include the irradiation unit and the display unit, or can further include the analysis unit, the irradiation unit, and the display unit.

Figure 7:
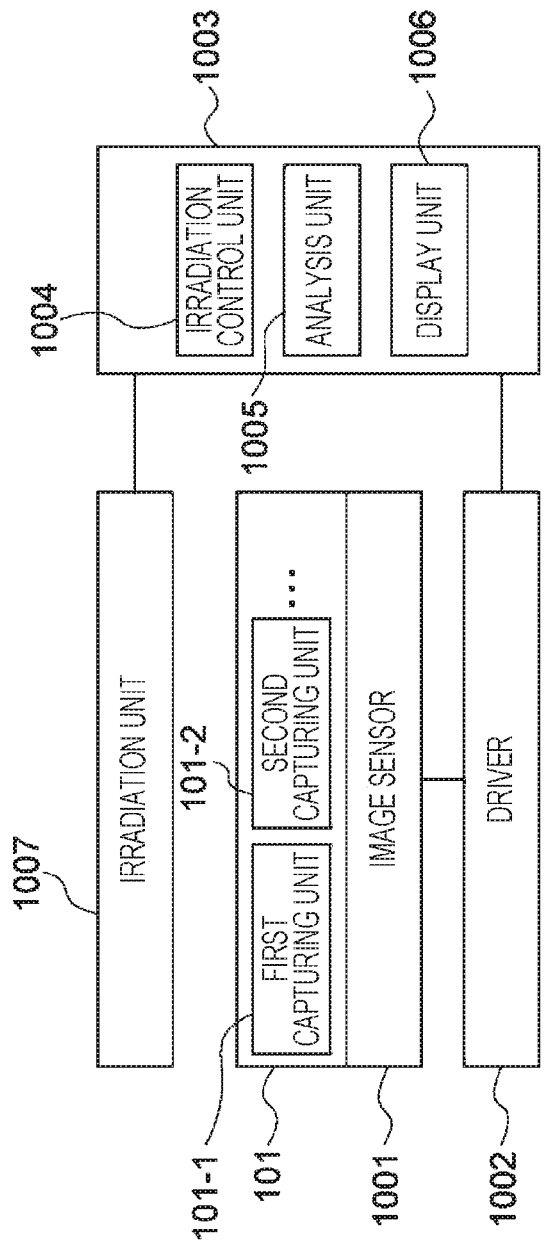
FIG. 7 is a block diagram illustrating a configuration example of a cell evaluation device according to a second embodiment to which the present technology is applied.

Refer to FIG. 7. A cell evaluation device 7 includes at least an image sensor upper portion 101 including a first capturing unit 101-1 and a second capturing unit 101-2, an image sensor 1001 (for example, a CMOS image sensor) that is an image acquisition unit, and an analysis unit 1005. In addition, the cell evaluation device 1 further includes a driver 1002, an irradiation control unit 1004, a display unit 1006, and an irradiation unit 1007. As illustrated in FIG. 1, the irradiation control unit 1004, the analysis unit 1005, and the display unit 1006 may be formed as one device 1003. Although not illustrated in FIG. 7, the image sensor upper portion 101 may include a protection unit in addition to the first capturing unit 101-1 and the second capturing unit 101-2.

In the cell evaluation device 7, above the image sensor 1001, the first capturing unit 101-1 (for example, a capturing unit including a first antibody for capturing a secretory substance) and the second capturing unit 101-2 (for example, a capturing unit including a second antibody for capturing cells) are disposed in a desired positional relationship. To identify cells captured by the second capturing unit 101-2, a cell image is captured using observation light of the cells or an irradiation unit 1007, and a cell size and a cell shape can be image-analyzed. A cell type and a cell state (for example, whether a cell is living or dead) can be accurately found. The cells are captured by the second capturing unit 101-2. Therefore, after the cells are cultured, for example, only a specific captured antibody (second antibody) that has reacted with a secretory substance is cleaved by an optical linker technique or the like, and the cells can be collected. In this case, a photodegradable linker is preferably included between the second capturing unit 101-2 and the image sensor 1001. Inclusion of a photodegradable linker allows only specific cells to be released. That is, the cell evaluation device 7 makes it possible to release the cells by irradiation with light after analysis of the cells and to take out only desired cells for post-analysis (gene analysis and the like).

In addition, cells are cultured above the image sensor 1001, and a secretory substance emitted from the cells is captured by the first capturing unit 101-1 (for example, a capturing unit including a first antibody for capturing the secretory substance). Thereafter, by further causing a reaction with a chemiluminescent substance and the like, weak light is generated, and the light can be acquired by the image sensor 1001 immediately below the first capturing unit 101-1. The chemiluminescent substance is, for example, an enzyme, and chemiluminescence is emitted by a reaction of the enzyme with a substrate.

The weak light is photoelectrically converted into an electric signal by the driver 1002, and the brightness of only a sensor portion where the secretory substance has been captured is increased. Therefore, the position where the secretory substance has been obtained above the image sensor 1001 can be mapped. Since a positional relationship between the first capturing unit 101-1 (for example, a capturing unit including a first antibody for capturing a secretory substance) and the second capturing unit 101-2 (for example, a capturing unit including a second antibody for capturing cells) can be designated in advance, a cell that has emitted a secretory substance can also be identified. Furthermore, the analysis unit 1005 can also quantify a secretory substance by utilizing a change in brightness depending on the concentration of the secretory substance. An image obtained from the image sensor 1001 is displayed on the display unit 1006 (for example, a monitor) through the analysis unit 1005.

Examples of measures for increasing sensitivity include an increase in the density of the first antibody for capturing the secretory substance included in the first capturing unit 101-1, minimizing a distance between the image sensor 1001 and the first capturing unit 101-1 (for example, an antibody layer) (disposing the first capturing unit 101-1 immediately above the image sensor 1001), an increase in exposure time, and separating a background noise portion and a signal portion from each other by image processing. In addition, acquisition of a cell image and detection of the secretory substance can also be performed in real time above the image sensor 1001.

3-2. First Capturing Unit and Second Capturing Unit, and Patterning of First Capturing Unit and Second Capturing Unit The cell evaluation device according to the second embodiment of the present technology includes a first capturing unit and a second capturing unit. As described above, the first capturing unit captures a secretory substance secreted by cells. The first capturing unit is as described in the section of the cell evaluation device according to the first embodiment (example 1 of cell evaluation device) of the present technology, and therefore detailed description thereof is omitted here.

The second capturing unit captures cells. The second capturing unit can include a molecule that is nonspecifically or specifically bonded to cells. The molecule that is nonspecifically or specifically bonded to the cells may be at least one selected from the group consisting of a second antibody, a second aptamer, a supramolecule, and oleylamine, and a plurality of types of the second antibodies may be included. A protection unit can be disposed in a region where the second capturing unit does not include the molecule that is nonspecifically or specifically bonded to the cells. The protection unit may include, for example, a collagen coat. Furthermore, the protection unit may include at least one type of hydrophilic polymer capable of suppressing adsorption of a biopolymer. Examples of the hydrophilic polymer include polyethylene glycol, a polymer having a phosphorylcholine group in a side chain thereof, a polysaccharide, a polypeptide, and the like.

Patterning of the first capturing unit and the second capturing unit will be described with reference to FIGS. 8A, 8B, 9A, 9B, 10A, and 10B. Referring to FIG. 8A, in the size 50 µm, a first capturing unit 402a is disposed around a second capturing unit 401a, and a protection unit 403a is disposed between the first capturing unit 402a and the second capturing unit 401a. FIG. 8B illustrates 16 pieces of patterning each including one first capturing unit and one second capturing unit illustrated in FIG. 8A. The second capturing unit 401a illustrated in FIG. 8A corresponds to a second capturing unit 401b illustrated in FIG. 8B, the first capturing unit 402a illustrated in FIG. 8A corresponds to a second capturing unit 402b illustrated in FIG. 8B, and the protection unit 403a illustrated in FIG. 8A corresponds to a second protection unit 403b illustrated in FIG. 8B.

Note that the cell evaluation device according to the first embodiment (example 1 of cell evaluation device) of the present technology does not include the second capturing unit 401a, and therefore has the first capturing unit 402a disposed in the portion of the second capturing unit 401a.

Referring to FIG. 9A, in the size 50 µm, first capturing units 502a to 505a are disposed around a second capturing unit 501a, and a protection unit 506a is disposed between the first capturing units 502a to 505a and the second capturing unit 501a and among the first capturing units 502a to 505a. The first capturing units 502a and 503a include the same material (for example, a first antibody), the first capturing unit 503a and 504a include the same material (for example, a first aptamer), and two types of materials are used. Regarding the first capturing units 502a to 505a, in FIG. 9A, the first capturing units 502a and 503a each have a vertically rectangular shape (longitudinal direction is the vertical direction in FIG. 9A), the first capturing units 504a and 505a each have a horizontally rectangular shape (longitudinal direction is the horizontal direction in FIG. 9A), and the first capturing units containing different materials are adjacent to each other. FIG. 9B illustrates 16 pieces of patterning each including one first capturing unit and one second capturing unit illustrated in FIG. 9A.

The second capturing unit 501a illustrated in FIG. 9A corresponds to the second capturing unit 501b illustrated in FIG. 9B, the first capturing unit 502a illustrated in FIG. 9A corresponds to the second capturing unit 502b illustrated in FIG. 9B, the first capturing unit 503a illustrated in FIG. 9A corresponds to the second capturing unit 503b illustrated in FIG. 9B, the first capturing unit 504a illustrated in FIG. 9A corresponds to the second capturing unit 504b illustrated in FIG. 9B, the first capturing unit 505a illustrated in FIG. 9A corresponds to the second capturing unit 505b illustrated in FIG. 9B, and the protection unit 506a illustrated in FIG. 9A corresponds to the protection unit 506b illustrated in FIG. 9B.

Note that the cell evaluation device according to the first embodiment (example 1 of cell evaluation device) of the present technology does not include the second capturing unit 501a, and therefore has at least one of the first capturing units 502a to 505a disposed in the portion of the second capturing unit 501a.

Referring to FIG. 10A, in the size 50 µm, first capturing units 602a to 609a are disposed around a second capturing unit 601a, and a protection unit 610a is disposed between the first capturing units 602a to 609a and the second capturing unit 601a and among the first capturing units 602a to 609a. The first capturing units 602a to 609a contain different materials from each other (for example, eight types of first antibodies or eight types of first aptamers), and use eight types of materials. The eight square-shaped first capturing units 602a to 609a are disposed in FIG. 10A. FIG. 10B illustrates 16 pieces of patterning each including one first capturing unit and one second capturing unit illustrated in FIG. 10A.

The second capturing unit 601a illustrated in FIG. 10A corresponds to the second capturing unit 601(b) illustrated in FIG. 10B, the first capturing unit 602a illustrated in FIG. 10A corresponds to the second capturing unit 602b illustrated in FIG. 10B, the first capturing unit 603a illustrated in FIG. 10A corresponds to the second capturing unit 603b illustrated in FIG. 10B, the first capturing unit 604a illustrated in FIG. 10A corresponds to the second capturing unit 604b illustrated in FIG. 10B, the first capturing unit 605a illustrated in FIG. 10A corresponds to the second capturing unit 605b illustrated in FIG. 9B, the first capturing unit 606a illustrated in FIG. 10A corresponds to the second capturing unit 606b illustrated in FIG. 10B, the first capturing unit 607a illustrated in FIG. 10A corresponds to the second capturing unit 607b illustrated in FIG. 10B, the first capturing unit 608a illustrated in FIG. 10A corresponds to the second capturing unit 608b illustrated in FIG. 10B, the first capturing unit 609a illustrated in FIG. 10A corresponds to the second capturing unit 609b illustrated in FIG. 9B, and the protection unit 610a illustrated in FIG. 10A corresponds to the protection unit 610b illustrated in FIG. 9B. Note that the cell evaluation device according to the first embodiment (example 1 of cell evaluation device) of the present technology does not include the second capturing unit 601a, and therefore has at least one of the first capturing units 602a to 609a disposed in the portion of the second capturing unit 601a.

3-3. Image Acquisition Unit, Analysis Unit, Irradiation Unit, and Display Unit The image acquisition unit included in the cell evaluation device according to the second embodiment (example 2 of cell evaluation device) of the present technology is as described in the section of the cell evaluation device according to the first embodiment (example 1 of cell evaluation device) of the present technology, and therefore detailed description thereof is omitted here. Furthermore, the analysis unit, the irradiation unit, and the display unit which can be included in the cell evaluation device according to the second embodiment (example 2 of cell evaluation device) of the present technology are also as described in the section of the cell evaluation device according to the first embodiment (example 1 of cell evaluation device) of the present technology, and therefore detailed description thereof is omitted here.

4. Third Embodiment (Example of Cell Evaluation System)

4-1. Cell Evaluation System

A cell evaluation system according to a third embodiment (example of cell evaluation system) of the present technology is a cell evaluation system including: a first capturing unit that captures a secretory substance secreted by cells; an image acquisition unit that acquires an image obtained by imaging observation light of the cells and light emitted from a luminescent substance bonded to the secretory substance; and an analysis unit that analyzes the obtained image, in which the image acquisition unit and the first capturing unit are disposed in this order, and the image acquisition unit acquires position information for the cells and the secretory substance.

Furthermore, the cell evaluation system according to the third embodiment (example of cell evaluation system) of the present technology may be a cell evaluation system including: a first capturing unit that captures a secretory substance secreted by cells; an image acquisition unit that acquires an image obtained by imaging observation light of the cells and light emitted from a luminescent substance bonded to the secretory substance; and an analysis unit that analyzes the obtained image, in which the image acquisition unit and the first capturing unit are disposed in this order, and the image acquisition unit acquires position information for the cells and the secretory substance.

The cell evaluation system according to the third embodiment of the present technology can further include at least one of an irradiation unit or a display unit. That is, the cell evaluation system according to the third embodiment of the present technology can further include the irradiation unit, can further include the display unit, or can further include the irradiation unit and the display unit.

Note that regarding the cell evaluation system according to the third embodiment of the present technology, except for the contents described above, the contents described in the sections of the cell evaluation devices according to the first and second embodiments of the present technology (examples 1 and 2 of cell evaluation device) can be directly applied to the cell evaluation system according to the third embodiment of the present technology.

4-2. First Capturing Unit, Second Capturing Unit, Image Acquisition Unit, Analysis Unit, Irradiation Unit, and Display Unit The image acquisition unit and the analysis unit included in the cell evaluation system according to the third embodiment (cell evaluation system) of the present technology is as described in the section of the cell evaluation device according to the first embodiment (example 1 of cell evaluation device) of the present technology, and therefore detailed description thereof is omitted here. Furthermore, the irradiation unit and the display unit which can be included in the cell evaluation system according to the third embodiment (cell evaluation system) of the present technology are also as described in the section of the cell evaluation device according to the first embodiment (example 1 of cell evaluation device) of the present technology, and therefore detailed description thereof is omitted here. Moreover, the second capturing unit that can be included in the cell evaluation system according to the third embodiment (cell evaluation system) of the present technology is as described in the section of the cell evaluation device according to the second embodiment (example 2 of cell evaluation device) of the present technology, and therefore detailed description thereof is omitted here.

Note that the embodiments of the present technology are not limited to the above-described embodiments, and various modifications can be made thereto without departing from the gist of the present technology.

Furthermore, the effects described here are merely examples, and the effects of the present technology are not limited thereto, and may include other effects.

Furthermore, the present technology can also have the following configurations [1] to [68].

[1]

A cell evaluation device including:
  a first capturing unit that captures a secretory substance secreted by cells; and
  an image acquisition unit that acquires an image obtained by imaging observation light of the cells and light emitted from a luminescent substance bonded to the secretory substance, in which
  the image acquisition unit and the first capturing unit are disposed in this order, and
  the image acquisition unit acquires position information for the cells and the secretory substance.

[2]

The cell evaluation device according to [1], in which the image acquisition unit is a CMOS image sensor.

[3]

The cell evaluation device according to [1] or [2], in which the image acquisition unit acquires an image obtained by imaging chemiluminescence emitted by a reaction of the luminescent substance that is an enzyme with a substrate.

[4]

The cell evaluation device according to any one of [1] to [3], in which the first capturing unit includes a molecule that is nonspecifically or specifically bonded to the secretory substance.

[5]

The cell evaluation device according to [4], in which a protection unit is disposed in a region where the first capturing unit does not include the molecule that is nonspecifically or specifically bonded to the secretory substance.

[6]

The cell evaluation device according to [4] or [5], in which the molecule that is nonspecifically or specifically bonded to the secretory substance is at least one selected from the group consisting of a first antibody, a first aptamer, and a molecular imprinted polymer.

[7]

The cell evaluation device according to [6], in which a plurality of types of the first antibodies is included.

[8]

The cell evaluation device according to any one of [1] to [7], further including a second capturing unit that captures the cells, in which
  the image acquisition unit and the second capturing unit are disposed in this order.

[9]

The cell evaluation device according to [8], in which the first capturing unit is disposed around the second capturing unit.

[10]
The cell evaluation device according to [8] or [9], in which a photodegradable linker is included between the second capturing unit and the image acquisition unit.
[11]
The cell evaluation device according to any one of [8] to [10], in which the second capturing unit includes a molecule that is nonspecifically or specifically bonded to the cells.
[12]
The cell evaluation device according to [11], in which a protection unit is disposed in a region where the second capturing unit does not include the molecule that is nonspecifically or specifically bonded to the cells.
[13]
The cell evaluation device according to [11] or [12], in which the molecule that is nonspecifically or specifically bonded to the cells is at least one selected from the group consisting of a second antibody, a second aptamer, a supramolecule, and oleylamine.
[14]
The cell evaluation device according to [13], in which a plurality of types of the second antibodies is included.
[15]
A cell evaluation device including:
 a first capturing unit that captures a secretory substance secreted by cells;
 an image acquisition unit that acquires an image obtained by imaging observation light of the cells and light emitted from a luminescent substance bonded to the secretory substance; and
 an analysis unit that analyzes the obtained image, in which
 the image acquisition unit and the first capturing unit are disposed in this order, and
 the image acquisition unit acquires position information for the cells and the secretory substance.
[16]
The cell evaluation device according to [15], in which the analysis unit quantifies the secretory substance on the basis of the intensity of the light emitted from the luminescent substance bonded to the secretory substance.
[17]
The cell evaluation device according to [15] or [16], in which the analysis unit analyzes the cells on the basis of brightness information of the observation light of the cells and/or the light emitted from the luminescent substance bonded to the secretory substance.
[18]
The cell evaluation device according to any one of [15] to [17], in which the image acquisition unit is a CMOS image sensor.
[19]
The cell evaluation device according to any one of [15] to [18], in which the image acquisition unit acquires an image obtained by imaging chemiluminescence emitted by a reaction of the luminescent substance that is an enzyme with a substrate.
[20]
The cell evaluation device according to any one of [15] to [19], in which the first capturing unit includes a molecule that is nonspecifically or specifically bonded to the secretory substance.
[21]
The cell evaluation device according to [20], in which a protection unit is disposed in a region where the first capturing unit does not include the molecule that is nonspecifically or specifically bonded to the secretory substance.

[22]
The cell evaluation device according to [20] or [21], in which the molecule that is nonspecifically or specifically bonded to the secretory substance is at least one selected from the group consisting of a first antibody, a first aptamer, and a molecular imprinted polymer.
[23]
The cell evaluation device according to [22], in which a plurality of types of the first antibodies is included.
[24]
The cell evaluation device according to any one of [15] to [23], further including a second capturing unit that captures the cells, in which
 the image acquisition unit and the second capturing unit are disposed in this order.
[25]
The cell evaluation device according to [24], in which the first capturing unit is disposed around the second capturing unit.
[26]
The cell evaluation device according to [24] or [25], in which a photodegradable linker is included between the second capturing unit and the image acquisition unit.
[27]
The cell evaluation device according to any one of [24] to [26], in which the second capturing unit includes a molecule that is nonspecifically or specifically bonded to the cells.
[28]
The cell evaluation device according to [27], in which a protection unit is disposed in a region where the second capturing unit does not include the molecule that is nonspecifically or specifically bonded to the cells.
[29]
The cell evaluation device according to [27] or [28], in which the molecule that is nonspecifically or specifically bonded to the cells is at least one selected from the group consisting of a second antibody, a second aptamer, a supramolecule, and oleylamine.
[30]
The cell evaluation device according to [29], in which a plurality of types of the second antibodies is included.
[31]
The cell evaluation device according to any one of [1] to [30], further including an irradiation unit that projects light onto the cells.
[32]
The cell evaluation device according to any one of [1] to [31], further including a display unit that displays the image.
[33]
The cell evaluation device according to [32], in which the display unit includes: a well image display unit based on a cell image image obtained by imaging observation light of the cells and a chemiluminescence image obtained by imaging light emitted from a luminescent substance bonded to the secretory substance; and an analysis data display unit and an analysis plot display unit based on analysis of the analysis unit.
[34]
A cell evaluation system including:
 a first capturing unit that captures a secretory substance secreted by cells; and
 an image acquisition unit that acquires an image obtained by imaging observation light of the cells and light emitted from a luminescent substance bonded to the secretory substance, in which
 the image acquisition unit and the first capturing unit are disposed in this order, and the image acquisition unit acquires position information for the cells and the secretory substance.

[35]
The cell evaluation system according to [34], in which the image acquisition unit is a CMOS image sensor.

[36]
The cell evaluation system according to [34] or [35], in which the image acquisition unit acquires an image obtained by imaging chemiluminescence emitted by a reaction of the luminescent substance that is an enzyme with a substrate.

[37]
The cell evaluation system according to any one of [34] to [36], in which the first capturing unit includes a molecule that is nonspecifically or specifically bonded to the secretory substance.

[38]
The cell evaluation system according to [37], in which a protection unit is disposed in a region where the first capturing unit does not include the molecule that is nonspecifically or specifically bonded to the secretory substance.

[39]
The cell evaluation system according to [37] or [38], in which the molecule that is nonspecifically or specifically bonded to the secretory substance is at least one selected from the group consisting of a first antibody, a first aptamer, and a molecular imprinted polymer.

[40]
The cell evaluation system according to [39], in which a plurality of types of the first antibodies is included.

[41]
The cell evaluation system according to any one of [34] to [40], further including a second capturing unit that captures the cells, in which
the image acquisition unit and the second capturing unit are disposed in this order.

[42]
The cell evaluation system according to [41], in which the first capturing unit is disposed around the second capturing unit.

[43]
The cell evaluation system according to [41] or [42], in which a photodegradable linker is included between the second capturing unit and the image acquisition unit.

[44]
The cell evaluation system according to any one of [41] to [43], in which the second capturing unit includes a molecule that is nonspecifically or specifically bonded to the cells.

[45]
The cell evaluation system according to [44], in which a protection unit is disposed in a region where the second capturing unit does not include the molecule that is nonspecifically or specifically bonded to the cells.

[46]
The cell evaluation system according to [44] or [45], in which the molecule that is nonspecifically or specifically bonded to the cells is at least one selected from the group consisting of a second antibody, a second aptamer, a supramolecule, and oleylamine.

[47]
The cell evaluation system according to [46], in which a plurality of types of the second antibodies is included.

[48]
A cell evaluation system including:
a first capturing unit that captures a secretory substance secreted by cells;
an image acquisition unit that acquires an image obtained by imaging observation light of the cells and light emitted from a luminescent substance bonded to the secretory substance; and
an analysis unit that analyzes the obtained image, in which
the image acquisition unit and the first capturing unit are disposed in this order, and
the image acquisition unit acquires position information for the cells and the secretory substance.

[49]
The cell evaluation system according to [48], in which the analysis unit quantifies the secretory substance on the basis of the intensity of the light emitted from the luminescent substance bonded to the secretory substance.

[50]
The cell evaluation system according to [48] or [49], in which the analysis unit analyzes the cells on the basis of brightness information of the observation light of the cells and/or the light emitted from the luminescent substance bonded to the secretory substance.

[51]
The cell evaluation system according to any one of [48] to [50], in which the image acquisition unit is a CMOS image sensor.

[52]
The cell evaluation system according to any one of [48] to [51], in which the image acquisition unit acquires an image obtained by imaging chemiluminescence emitted by a reaction of the luminescent substance that is an enzyme with a substrate.

[53]
The cell evaluation system according to any one of [48] to [52], in which the first capturing unit includes a molecule that is nonspecifically or specifically bonded to the secretory substance.

[54]
The cell evaluation system according to [53], in which a protection unit is disposed in a region where the first capturing unit does not include the molecule that is nonspecifically or specifically bonded to the secretory substance.

[55]
The cell evaluation system according to [53] or [54], in which the molecule that is nonspecifically or specifically bonded to the secretory substance is at least one selected from the group consisting of a first antibody, a first aptamer, and a molecular imprinted polymer.

[56]
The cell evaluation system according to [55], in which a plurality of types of the first antibodies is included.

[57]
The cell evaluation system according to any one of [48] to [56], further including a second capturing unit that captures the cells, in which
the image acquisition unit and the second capturing unit are disposed in this order.

[58]
The cell evaluation system according to [57], in which the first capturing unit is disposed around the second capturing unit.

[59]
The cell evaluation system according to [57] or [58], in which a photodegradable linker is included between the second capturing unit and the image acquisition unit.

[60]
The cell evaluation system according to any one of [57] to [59], in which the second capturing unit includes a molecule that is nonspecifically or specifically bonded to the cells.

[61]
The cell evaluation system according to [60], in which a protection unit is disposed in a region where the second capturing unit does not include the molecule that is nonspecifically or specifically bonded to the cells.

[62]
The cell evaluation system according to [60] or [61], in which the molecule that is nonspecifically or specifically bonded to the cells is at least one selected from the group consisting of a second antibody, a second aptamer, a supramolecule, and oleylamine.

[63]
The cell evaluation system according to [62], in which a plurality of types of the second antibodies is included.

[64]
The cell evaluation system according to any one of [34] to [63], further including an irradiation unit that projects light onto the cells.

[65]
The cell evaluation system according to any one of [34] to [64], further including a display unit that displays the image.

[66]
The cell evaluation system according to [65], in which the display unit includes: a well image display unit based on a cell image image obtained by imaging observation light of the cells and a chemiluminescence image obtained by imaging light emitted from a luminescent substance bonded to the secretory substance; and an analysis data display unit and an analysis plot display unit based on analysis of the analysis unit.

[67]
A cell evaluation device including:
a first antibody that captures a secretory substance secreted by cells;
a second antibody that captures the cells; and
a CMOS image sensor that acquires an image obtained by imaging observation light of the cells and light emitted from a luminescent substance bonded to the secretory substance, in which
the CMOS image sensor, the first antibody, and the second antibody are disposed in this order,
the first antibody is disposed around the second antibody, and
the CMOS image sensor acquires position information for the cells and the secretory substance.

[68]
A cell evaluation device including:
a first antibody that captures a secretory substance secreted by cells;
a second antibody that captures the cells;
a CMOS image sensor that acquires an image obtained by imaging observation light of the cells and light emitted from a luminescent substance bonded to the secretory substance; and
an analysis unit that analyzes the acquired image, in which
the CMOS image sensor, the first antibody, and the second antibody are disposed in this order,
the first antibody is disposed around the second antibody, and
the CMOS image sensor acquires position information for the cells and the secretory substance.

[69]
A cell evaluation system including:
a first antibody that captures a secretory substance secreted by cells;
a second antibody that captures the cells; and
a CMOS image sensor that acquires an image obtained by imaging observation light of the cells and light emitted from a luminescent substance bonded to the secretory substance, in which
the CMOS image sensor, the first antibody, and the second antibody are disposed in this order,
the first antibody is disposed around the second antibody, and
the CMOS image sensor acquires position information for the cells and the secretory substance.

[70]
A cell evaluation system including:
a first antibody that captures a secretory substance secreted by cells;
a second antibody that captures the cells;
a CMOS image sensor that acquires an image obtained by imaging observation light of the cells and light emitted from a luminescent substance bonded to the secretory substance; and
an analysis unit that analyzes the acquired image, in which
the CMOS image sensor, the first antibody, and the second antibody are disposed in this order,
the first antibody is disposed around the second antibody, and
the CMOS image sensor acquires position information for the cells and the secretory substance.

REFERENCE SIGNS LIST

1 Cell evaluation device
101-1 First capturing unit
101-2 Second capturing unit
1001 Image acquisition unit (image sensor)
1005 Analysis unit
1006 Display unit

The invention claimed is:
1. A cell evaluation device, comprising:
a first capturing device configured to capture a secretory substance secreted by cells, wherein
the first capturing device includes a first molecule that is nonspecifically bonded to the secretory substance, and
the first molecule is at least one selected from a group consisting of a first aptamer and a molecular imprinted polymer;
a second capturing device configured to capture the cells, wherein
the second capturing device includes a second molecule that is nonspecifically bonded to the cells, and
the second molecule is at least one selected from a group consisting of a supramolecule and oleylamine; and
an image sensor configured to:
acquire a first image by a first imaging process of observation light of the cells and light emitted from a luminescent substance bonded to the secretory substance,
wherein the first capturing device is on the image sensor; and acquire, based on the first image, position information of the cells and the secretory substance.

2. The cell evaluation device according to claim 1, wherein the image sensor is a CMOS image sensor.

3. The cell evaluation device according to claim 1, wherein the image sensor is further configured to acquire a second image by a second imaging process of chemiluminescence emitted by a reaction of the luminescent substance that is an enzyme with a substrate.

4. The cell evaluation device according to claim 1, further comprising a protection section in a region where the first capturing device does not include the first molecule that is nonspecifically bonded to the secretory substance.

5. The cell evaluation device according to claim 1, wherein the first molecule that is nonspecifically bonded to the secretory substance is a first antibody.

6. The cell evaluation device according to claim 5, wherein the first capturing device further includes a plurality of types of the first antibody.

7. The cell evaluation device according to claim 1, wherein the second capturing device is on the image sensor.

8. The cell evaluation device according to claim 7, wherein the first capturing device is around the second capturing device.

9. The cell evaluation device according to claim 1, further comprising a protection section in a region where the second capturing device does not include the second molecule that is nonspecifically bonded to the cells.

10. The cell evaluation device according to claim 1, wherein the second molecule is at least one selected from a group consisting of a second antibody and a second aptamer.

11. The cell evaluation device according to claim 10, wherein the second capturing device further includes a plurality of types of the second antibody.

12. A cell evaluation system, comprising:
a first capturing device configured to capture a secretory substance secreted by cells, wherein
the first capturing device includes a first molecule that is nonspecifically bonded to the secretory substance, and
the first molecule is at least one selected from a group consisting of an aptamer and a molecular imprinted polymer;
a second capturing device configured to capture the cells, wherein
the second capturing device includes a second molecule that is nonspecifically bonded to the cells, and
the second molecule is at least one selected from a group consisting of a supramolecule and oleylamine;
an image sensor configured to:
acquire an image by an imaging process of observation light of the cells and light emitted from a luminescent substance bonded to the secretory substance; and
acquire, based on the image, position information of the cells and the secretory substance,
wherein the first capturing device is on the image sensor; and
a projector configured to project light onto the cells.

13. The cell evaluation device according to claim 1, further comprising a photodegradable linker between the image sensor and the second capturing device.

14. The cell evaluation system according to claim 12, further comprising a display screen configured to display the image.

15. The cell evaluation system according to claim 14, wherein
the display screen is further configured to display a well image, based on a cell image and a chemiluminescence image,
the cell image is based on the observation light of the cells, and
the chemiluminescence image is based on the light emitted from the luminescent substance bonded to the secretory substance.

* * * * *